United States Patent [19]

Rydell et al.

[11] Patent Number: 5,258,006
[45] Date of Patent: Nov. 2, 1993

[54] BIPOLAR ELECTROSURGICAL FORCEPS

[75] Inventors: Mark A. Rydell, Golden Valley; Corey J. Kulseth, Minnetonka, both of Minn.

[73] Assignee: Everest Medical Corporation, Minneapolis, Minn.

[21] Appl. No.: 933,127

[22] Filed: Aug. 21, 1992

[51] Int. Cl.5 .............................................. A61B 17/42
[52] U.S. Cl. ............................. 606/205; 606/32; 606/40; 606/49; 606/50; 606/51; 606/52
[58] Field of Search ................ 606/32, 37, 39, 40, 606/41, 45, 46, 47, 48, 49, 50, 51, 52, 79, 167, 170, 171, 151, 175, 174, 205, 206

[56] References Cited

U.S. PATENT DOCUMENTS

| | | |
|---|---|---|
| 3,920,021 | 11/1975 | Hiltebrandt . |
| 4,003,380 | 1/1977 | Wien ........................ 606/51 |
| 4,005,714 | 2/1977 | Hiltebrandt ............... 606/51 |
| 4,452,546 | 6/1984 | Hiltebrandt et al. . |
| 4,461,305 | 7/1984 | Cibley ........................ 128/751 |
| 4,532,924 | 8/1985 | Auth et al. . |
| 4,977,900 | 12/1990 | Fehling et al. ............. 128/751 |
| 5,009,661 | 4/1991 | Michelson ................. 606/170 |
| 5,078,717 | 1/1992 | Parins et al. .............. 606/48 |

FOREIGN PATENT DOCUMENTS

| | | |
|---|---|---|
| 0517244 | 12/1992 | European Pat. Off. . |
| 0518230 | 12/1992 | European Pat. Off. . |
| 2808911 | 3/1979 | Fed. Rep. of Germany ........ 606/79 |
| 3709067 | 9/1988 | Fed. Rep. of Germany ...... 606/205 |
| 649420 | 3/1979 | U.S.S.R. ................... 606/79 |

OTHER PUBLICATIONS

U.S. Sir H1028, Mar. 3, 1992, Falk et al.

Primary Examiner—C. Fred Rosenbaum
Assistant Examiner—Noelle Kent Gring
Attorney, Agent, or Firm—Haugen and Nikolai

[57] ABSTRACT

An instrument for cauterizing blood vessels while performing an endoscopic procedure includes a rigid outer tube with a proximal end, a distal end and an inner, semi-rigid, tube passing through the outer tube from its proximal end to its distal end. The inner tube has at least one lumen allowing passage of a pair of conductive leads therethrough. The leads terminate at the distal end of the tube in a pair of forceps jaws. The leads are mechanically connected to a scissors-style handle and are electrically connected to an RF generator. The outside diameter of the outer tubular body is sufficiently small that it can readily pass through the working lumen of an endoscope. Associated with the handle is a knob for rotating the inner tube and the conductive leads. The handle also contains a means for effecting translational motion of the inner tube within the outer tube and over the forceps and a means for introducing a preset gap to prevent complete closure of the forceps' jaws.

14 Claims, 1 Drawing Sheet

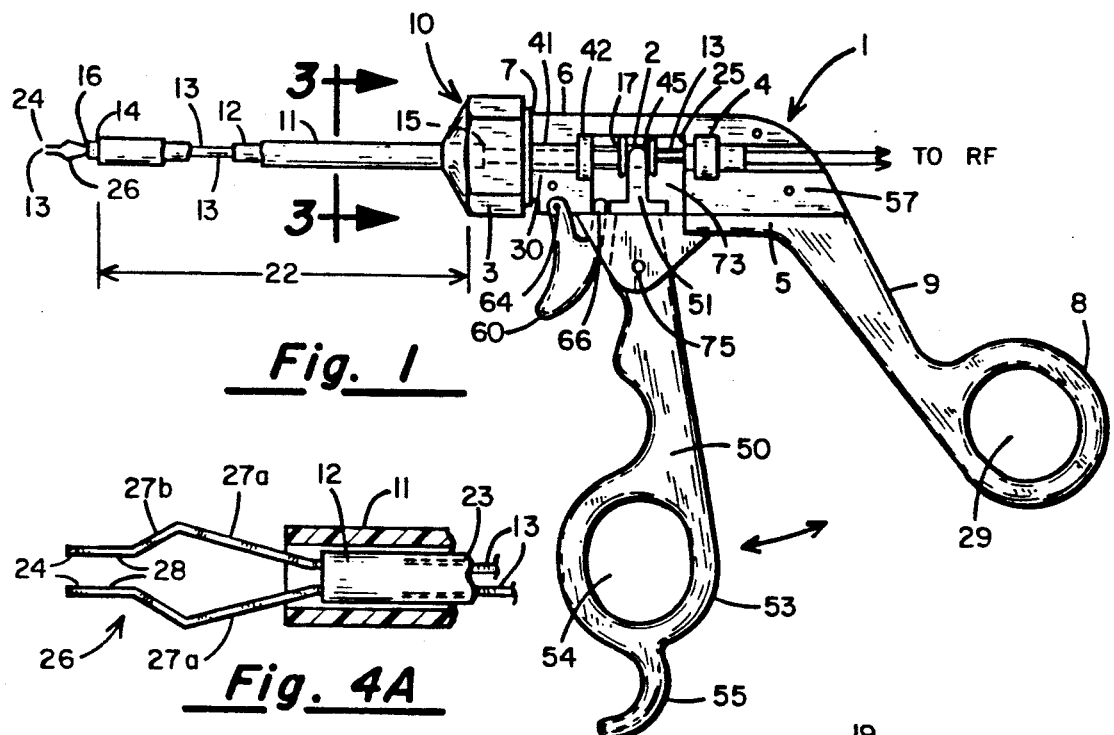
Fig. 1
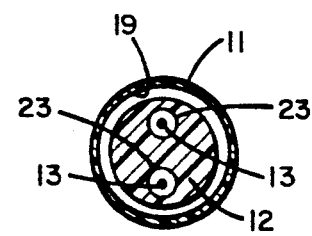
Fig. 4A
Fig. 4B
Fig. 3
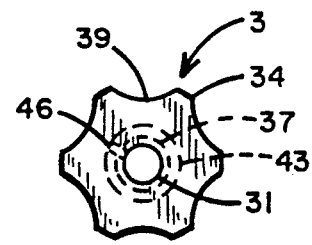
Fig. 5
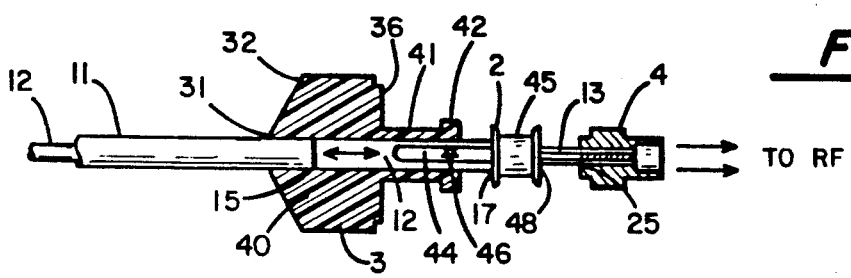
Fig. 2

BIPOLAR ELECTROSURGICAL FORCEPS

BACKGROUND OF THE INVENTION

I. Field of the Invention

This invention relates generally to electrosurgical instruments, and more particularly to a bipolar electrosurgical forceps cauterization instrument specifically designed for use in the performance of percutaneous laparoscopic cholecystectomy or similar endoscopic procedures.

II. Discussion of the Prior Art

Heat has been used for the cauterization of bleeding wounds for centuries. Recently, the use of radio frequency (RF) energy travelling through the body has been widely used to stop bleeding. The RF energy cauterizes the blood vessels by heating proteins in the blood to a temperature where the proteins congeal. RF energy is preferred because its frequency is above that which could otherwise cause neuro-muscular stimulation. At least two modes of RF cauterization are typically employed, namely monopolar or bipolar coagulation.

A monopolar electrosurgical system usually consists of an RF generator unit, an active electrode of small dimensions, and a large area return or dispersive electrode designed to be placed on the patient's buttocks or thigh to serve as a return point for the RF energy released at the active electrode site. The active electrode is applied to the bleeding site and the current path is completed through the body to the return electrode which is electrically in contact with the buttocks or thigh. One technique in which the monopolar mode may be employed involves fulguration which is the use of a spark or arc from the active electrode to the tissue.

Bipolar electrosurgical devices have the inherent advantage over monopolar devices of containing the RF energy. In a bipolar device, both the active and the return electrodes are placed on the surgical instrument. Thus, no separate return electrode on the patient is required as in monopolar systems. The RF energy remains at the site where the device is being used and only affects patient tissue in close proximity. Generally, bipolar devices are able to achieve the same results as competing monopolar devices while using a lower level of RF energy. Potential patient complications related to monopolar RF energy travelling through the body on a somewhat unpredictable path to the return electrode are avoided.

The conventional treatment for a diseased gall bladder has been a total cholecystectomy involving cutting a fairly large incision through the abdominal wall and, using a scalpel, to dissect the gall bladder from its bed and to cut a cystic artery and cystic duct to thereby release the organ and allow it to be extracted through the incision. According to *National Inpatient Profile, Health Care Knowledge Systems*, Ann Arbor, Mich., 1989: 360, the average post operative stay following gall bladder removal surgery of this type in 1988, on a nationwide basis, was 6.1 days and full recovery to normal activities required four to six weeks recuperation.

A relatively new procedure referred to as "laparoscopic laser cholecystectomy" has been devised and it is significantly less invasive than the heretofore conventional approach for gall bladder removal. Rather than working through a major incision in the abdominal wall, a first small puncture wound is made in the umbilicus. A needle is inserted and a pneumoperitoneum is established with $CO_2$ gas to distend the abdomen. Next, a trocar and cannula are inserted through the umbilical incision and following removal of the trocar, a diagnostic laparoscope is inserted. Rather than direct visualization through the laparoscope, the scene may be viewed on a CRT screen.

Upon proper observation of the peritoneal cavity, three additional incisions are made at predetermined locations and cannulas are inserted. The lumens and the cannulas are sufficiently large to permit surgical instruments to be inserted therethrough. The instruments generally include a grasping forceps, a clip plier for ligating the cystic duct and cystic artery, a microscissors and a coagulating or cauterizing instrument. A flexible, fiber-optic rod coupled to the output of the laser is used to effect hemostatic cutting and vaporization.

The percutaneous laparoscopic procedure allows total removal of the gall bladder through the larger cannula. Following the surgery all that is required is a single stitch in the umbilicus and the use of sterile adhesive strips for closing the other three wounds. Using this procedure, the hospital stay has been reduced to less than one day and the period for total recovery and resumption of normal activities is reduced to about 4 days. Moreover, scarring is minimal.

In the past, to cauterize blood vessels during the percutaneous laparoscopic cholecystectomy, either the cutting laser was used for small bleeding blood vessels, or a monopolar cauterization instrument was used for larger bleeders. These methods, however, have two significant drawbacks. Monopolar instruments, using RF energy, often have an unpredictable current flow path back to the return electrode. This unpredictable current flow may have a destructive effect on tissues surrounding the cystic duct or the cystic artery. While non-contact positioning of a bipolar laser may overcome this problem, the laser has no way of holding a bleeding vessel and is not used on larger bleeders. The invention described herein overcomes both of these drawbacks, by utilizing bipolar energy applied to a rotatable forceps that can hold a bleeding blood vessel or vessels.

U.S. Pat. No. 4,005,714, entitled "Bipolar Coagulation Forceps", describes an arrangement in which the forceps is designed to occlude both the fallopian tube and the adjacent mesosalpinx. The forceps embodies two insulated current conductors terminating in a coaxial plug and a coaxial contact bushing. The conductors may be opened and closed by shifting an outer actuating sleeve with the aid of a handle that is stationary in relation to the forceps' arms. The device moves the outer sleeve translationally in relation to the inner stationary sleeve and forceps device. In contrast, in the invention yet to be described herein an inner tube moves translationally within a stationary outer tube. The device of the '714 patent also differs from the current invention in that it has no means built into the handle for permitting rotation of the forceps' jaws or pinchers at the distal end of the tubes without turning the entire device and no means for introducing a preset gap between the forceps' jaws. The invention described herein incorporates the flexibility of a rotating forceps at the distal end of the tubes, while holding its handle stationary, to thereby better facilitate grasping bleeding blood vessels. The invention allows introduction of a present gap between the forceps' jaws to preclude shorting of the leads at the distal end and give better control over cauterization of bleeding tissues.

U.S. Pat. No. 3,920,021 describes devices for coagulating animal tissue by means of high frequency current. The device, as depicted, appears to show bipolar electrodes at the distal end of an outer tube. The proximal end of the outer tube and the proximal end of the inner tube are attached to a squeezable device that will move both the outer tube and the inner tube. Hence, neither the outer tube nor the inner tube is translationally stationary in relation to the handle. The device described in the '021 patent does not contain a means for rotating the forceps at the distal end while holding the handle stationary or means for introducing a preset gap between the forceps' jaws. As such, it is less than satisfactory for laparoscopic procedures.

From the above analysis, it can be seen that the prior art references, individually and as a whole, do not disclose a bipolar electrosurgical forceps cauterizing instrument for use in percutaneous laparoscopic cholecystectomy procedures having rotatable pinching electrodes, an inner tube which moves translationally in respect to a translationally stationary outer tube and handle mechanism or a trigger means for quickly and easily introducing a preset gap between the forceps' jaws.

SUMMARY OF THE INVENTION

The present invention is directed to a bipolar electrosurgical forceps instrument which is specifically designed to be insertable through a cannula for use in coagulating and cauterizing during the laparoscopic cholecystectomy procedure. Thus, the more inherently risky monopolar coagulation instruments and the presently inflexible bipolar coagulation instruments can be dispensed with and replaced with a disposable low-cost substitute.

It is accordingly a principal object of the present invention to provide an improved instrument for carrying out laparoscopic cauterization procedures within the abdominal cavity.

Another object of the invention is to provide an improved electrosurgical instrument for performing cauterization procedures during a laparoscopic cholecystectomy.

Yet another object of the invention is to provide a bipolar electrosurgical instrument allowing better control over the location where cauterization is intended, than can be achieved with monopolar electrosurgical instruments.

Yet another object of the invention is to provide a bipolar electrosurgical instrument that has rotatable forceps jaws that allow better control over the grasping of bleeding blood vessels for cauterization than can be achieved with electrosurgical instruments that must be turned as a whole to effect rotation of the forceps' jaws.

Yet another object of the invention is to provide a bipolar electrosurgical instrument with a means for quickly and easily introducing a preset gap between the forceps' jaws to preclude shorting of the leads and give better control over cauterization of bleeding tissue.

The foregoing, features and advantages of the present invention are attained by providing an electrosurgical instrument comprising a generally rigid outer tube having a proximal end, a distal end, and an inner semi-rigid tube passing through the outer tube where the inner tube has a proximal end and a distal end corresponding to the outer tube's proximal and distal ends. The inner tube has lumen means extending from the proximal end to the distal end for allowing passage of two conductive leads, with each lead in a separate lumen. The leads are, thus, insulated from each other by the inner tube along their length until they protrude out of the distal end of the inner tube and outer tube where they are bent to form the pinchers or jaws of the forceps. The outside diameter of the outer tube is sufficiently small to permit it to be passed through a cannula percutaneously positioned through the abdominal wall. The length of the rigid outer tube is sufficient to permit the bipolar electrodes comprising the jaws, protruding out of the distal end, to reach the bleeding blood vessels to be cauterized when the instrument is inserted through the cannula.

To prevent loss of $CO_2$, used to distend the abdominal cavity making more room to work in, a silicone grease may be applied near the proximal end of the inner and outer tubes. The grease forms an effective seal between the inner and the outer tube, and between the leads and the inner tube. This allows the inner tube to move longitudinally in the outer tube and the leads to slide within the inner tube, while maintaining a seal.

The jaws of the bipolar forceps are spaced apart and therefore open when the leads are extended a predetermined distance beyond the distal end of the inner tube. When the inner tube is advanced coaxially in the distal direction within the lumen of the outer tube, the distal end of the inner tube squeezes the protruding forceps' jaws together. The conductive leads protruding out of the proximal end of the instrument are adapted to be connected to a high frequency generator which, when turned on, causes energy to flow between the electrodes comprising the forceps' jaws, cauterizing the blood vessel or vessels pinched between them.

The electrosurgical instrument of the present invention further has a handle member that contains a means for rotating the inner tube, the forceps' jaws, and the outer tube while maintaining the handle stationary. The handle further contains a means for translationally moving the inner tube within the lumen of the outer tube. In the preferred embodiment of the device, the means for rotating the inner tube, the forceps' jaws, and the outer tube is a knob located at the proximal end of the tubes and the distal end of the handle. The knob is of a first diameter but has an inner extension of a lesser diameter coupled by a spline connection to the inner tube. When the knob is rotated by the user the inner tube, the outer tube and the conductors terminating in the forceps' jaws rotate while the handle grip remains fixed in position. Translational motion of the inner tube within the outer tube is accomplished by fixing the outer tube to the knob and handle and connecting the inner tube to an arm that is pivotally attached to the main body of the handle. When the pivotally attached arm is moved in a scissors-like manner, the inner tube is made to move reciprocally within the lumen of the outer tube.

To preclude shorting of the forceps' jaws and to give better control over cauterization of bleeding tissue, the handle contains a finger activated safety catch or trigger. The trigger, when pulled, introduces a piece of plastic between the pivotally mounted arm and the handle frame. This stops the arm from effecting further translational motion of the inner tube within the lumen of the outer tube and stops the forceps' jaws from closing.

Other objects, features and advantages of the present invention will become apparent to those skilled in the art through the Description of the Preferred Embodiment, claims, and drawings herein.

BRIEF DESCRIPTION OF THE DRAWINGS

FIG. 1 is a partially sectioned, side elevation of a bipolar electrosurgical forceps cauterization instrument configured in accordance with the preferred embodiment of the invention;

FIG. 2 is a partially vertical sectioned, side elevation of a rotating knob, the proximal end of an outer tube, a free wheeling electrical connector, the proximal end of the conductive leads, and the proximal end of an inner tube with a groove and spool configuration, showing the spline connection of the rotatable knob to the inner tube;

FIG. 3 is a cross-sectional view of the outer tube, inner tube and the two lumens that extend through the inner tube taken along the line 3—3 in FIG. 1;

FIG. 4A is a partially sectioned close-up view of the distal end of the bipolar forceps with the jaws open;

FIG. 4B is a partially sectioned, close-up view of the distal end of the bipolar forceps with the jaws closed; and FIG. 5 is a front-end view of the rotatable knob.

DESCRIPTION OF THE PREFERRED EMBODIMENT

Indicated generally in FIG. 1 is an electrosurgical cauterizing instrument 10 designed for use as a cauterizing forceps in percutaneous laparoscopic cholecystectomy procedures. The electrosurgical cauterizing instrument 10 generally comprises an elongated, rigid outer tubular member 11, an elongated, semi-rigid inner tubular member 12, a pair of conductive leads 13, and a scissors-style handle member indicated generally by numeral 1. In general, the handle frame is made out of a medical grade plastic, such as a 20% glass filled polycarbonate material.

As indicated in FIGS. 1 and 3, the rigid outer tube 11, preferably made from stainless steel or glass fiber reinforced plastic, has a distal end 14, a proximal end 15, and an inner tube 12 passing coaxially through the central lumen of the outer tube 11. The inner tube 12 is preferably made from an insulating material such as silastic or polyurethane and has a distal end 16 and a proximal end 17. The outside diameter of the inner tube 12 is small enough to fit loosely inside the lumen 19 of the outer tube 11. This allows the inner tube 12 to translationally slide inside the outer tube 11. The outside diameter of the outer tube 11 is small enough to pass through a cannula and the length 22 is sufficient to reach an internal blood vessel to be cauterized when the inner tube 12 and the outer tube 11 are together slidably inserted through the abdominal wall via the cannula. To prevent loss of insufflation fluid, e.g., $CO_2$ used for distending the abdominal cavity, a silicone gel is applied near the proximal end 15 of the outer tube 11 and the proximal end 17 of the inner tube 12. This creates a seal between the inner tube 12 and the outer tube 11, and the inner tube 12 and leads 13 while allowing each to slide within the other.

The distal end 16 of the inner tube 12 generally aligns with or is slightly recessed with respect to the distal end 14 of the outer tube 11 when the jaws of the forceps are open relative to one another (FIG. 4A), while the proximal end 17 of the inner tube 12 protrudes out of the proximal end 15 of the outer tube 11 and into the handle 1 (FIG. 1). The inner tube 12 has a pair of lumens 23 (FIG. 3) that extend the entire length thereof.

The pair of conductive leads 13 extend the entire length of the inner tube 12 through the pair of lumens 23. The leads 13 have a first zone which are free of insulation and that are preferably flattened to form bipolar electrode surfaces 28 on the forceps' jaws 26, and a proximal end 25 that terminates in a free-wheeling connector 4. The free-wheeling connector 4 cannot move translationally in the handle 1 but can freely rotate.

Contiguous to the flat, insulation-free electrodes in a second zone, the leads 13 are bent away from each other as at 27(a), back together as at 27(b) and then again parallel to one another. As seen in FIGS. 4A and 4B, this forms the jaws of the forceps at the distal ends of the leads 13 and a ramp surface engagable by the distal end of the inner tube 12. The forceps' jaws 26 are flattened and serrated on surfaces 28 to form a gripping surface. The forceps' jaws 26 are not insulated from one another, except by the air gap existing when the jaws are open. The squeezing action of the jaws 26 is accomplished by moving the inner tube 12 in the distal direction inside the lumen of the outer tube 11. The leads 13 are fastened to the free-wheeling connector 4, which cannot move translationally, so the inner tube 12 slides over them, relative to the stationary conductive leads 13.

The inner tube 12 is made to move translationally inside the outer tube 11 and over the leads 13 by effecting longitudinal displacement of a slidable spool mechanism 2 located inside the handle 1. As shown in FIGS. 4A and 4B, when the inner tube 12 is pushed over the forceps' jaws 26 by manipulating the scissors-style handle which is operatively coupled to the slidable spool mechanism 2, the material forming the distal end of the inner tube 12 is forced against the angular bend 27(a) of the forceps 26 causing the forceps' jaws 26 to close. The portion of the leads 13 comprising the angular bends 27(a) and 27(b) may be appropriately insulated so as not to short together when in contact with the outer tube 11 if made of stainless steel. When the inside tube 12 is retracted by the scissor mechanism comprising handle 1 and slidable spool mechanism 2 contained therein, the conductive leads 13 extend sufficiently beyond the distal end 16 of the inner tube 12 so as not to engage the ramps 27(a) and the forceps' jaws 26 will become separated, due to the memory property of the conductive leads 13.

With reference to FIGS. 1 and 2, the proximal ends 25 of the conductive leads 13 extend beyond the proximal end 17 of the inner tube 12 and connect to the free wheeling rotatable electrical connector 4 located in the handle 1. The connector 4 cannot move longitudinally in the handle 1 by virtue of its being contained in a recess formed in the handle. The electrical connector 4 is used to join external leads of an electrosurgical generator to the conductors 13 of the instrument 10. When the jaws 26 of the forceps are squeezed together, the high frequency generator, activated independently by the user, transmits RF energy through the conductive leads 13 to the bipolar electrode surfaces 28 of the jaws 26 to cauterize the blood vessel or vessels squeezed therebetween. Cauterization occurs due to the heat transferred to the blood by the RF energy as it propagates between forceps' jaws 26. As shown in FIG. 1, in the preferred embodiment, the stationary handle is made in two halves 5, each having a longitudinally extending section 6 that terminates at the handle's distal end 7 in a connection 30 with the rotatable knob 3. The proximal end 8 of the handle frame halves 5 terminate in a downward sloping arm 9 that terminates in an annular, finger-receiving opening 29.

As seen in FIGS. 2 and 5, the rotatable knob 3 is generally cylindrical in shape, having a bore 31 through its center along the central axis. The bore 31 is large enough to accept the outer tube 11 therein and allow the inner, tube 12 to pass through its lumen. The proximal end 15 of the outer tube 11 is frictionally inserted into the bore 31 of the rotatable knob 3. The front surface 32 of the rotatable knob 3 slopes upwardly and rearwardly from the bore 31. The rotatable knob 3 has regularly spaced arcuate indentations 39 around its outer diameter 34, allowing a user to readily grip the knob 3 even if slippery from body fluids. The proximal end surface 36 of the rotatable knob 3 abuts the distal end 7 of the handle frame halves 5.

Extending out of the proximal end surface 36 of the rotatable knob 3 is an integrally formed tubular extension 41 having a smaller outer diameter 37 (FIG. 5) than the outer diameter 34 of the knob's main body 40. At the end of the extension 41, opposite the knob's main body 40, is an annular flange 42 with a slightly larger diameter 43 than the outer diameter 37 of the extension, but a smaller diameter than the knob's main body diameter 34. As seen in FIG. 1, the knob extension 41 and the flange 42 fit inside the handle frame halves 5 at the handle frame's distal end 7. The handle frame halves 5 are eventually attached together in sandwich fashion to enclose the handle 1 and hold the rotatable knob 3 with extension 41 in place. The rotatable knob 3 and the extension 41 are preferably made out of nylon so the extension 41 can be a lubricous bearing for smoother rotation of the knob 3 inside of the handle frame halves 5. The flange 42 of the knob 3 has a hole 46 running perpendicular to the knob's central axis from the outside diameter 43 to the bore 31. The bore 31 passes through the rotatable knob 3, tubular extension 41, and the flange 42.

The proximal end 17 of the inner tube 12 extends beyond the proximal end of the outer tube 11 and completely through the knob bore 31. Extending along the proximal end portion 17 of the inner tube 12 is a longitudinal groove 44 which runs along the inner tube 12 parallel to its central axis. The groove 44 runs to a spool 45 at the proximal end 17 of the inner tube 12. A screw or pin, inserted into the hole 46 in the flange 42, protrudes into the groove 44 of the inner tube 12 making a spline connection. The pin does not securely fasten the knob 3 to the inner tube 12. Instead, the spline connection allows the inner tube 12 to be translated inside the outer tube 11 and knob 3 while still effectively connecting the knob 3 to the inner tube 12 so when the knob 3 is rotated the inner tube 12 and forceps' jaws 26 will rotate. The spool 45 and inner tube 12 are frictionally fit together. The spool 45 is cylindrical along the central axis of the inner tube 12 and has two end flanges 48, one at each end.

The spool 45 is part of the slidable spool mechanism 2 used for reciprocally moving the inner tube 12 longitudinally within the translationally stationary outer tube 11 and knob 3. The other part of the slidable spool mechanism 2 is a pivotally mounted lever arm 50 secured by a pivot pin to the stationary handle frame halves 5 on the section 6 just below a slot 73 formed in the frame 5. The slot 73 is large enough to accommodate the spool 45 and a bifurcated end 51 of the pivotally mounted arm 50. The bifurcated end 51 engages opposing side surfaces of the spool 45 between the spool's two flanges 48. The coupling allows the spool 45, inner tube 12 and conductive leads 13 to rotate. The bifurcated end 51 contacts the flanges 48 of the spool 45 when the arm 50 is manipulated, thus, moving the spool 45 and inner tube 12 back and forth longitudinally.

As shown, the bottom grip on arm 50 comprises a hole 54 for a finger and a downward protruding hook 55 for another finger. The hook 55 curves toward the distal end 7 of the handle frame 5 when the movable arm element 50 is pivotally mounted to the stationary frame element 5 at pin location 75. By pulling the bottom grip 53 toward the stationary handle 9, the bifurcated end 51 of the pivotally mounted movable arm element 50 moves toward the distal end 7 of the handle frame 5 and thereby urges the spool 45 toward the distal end 7 of the handle 1. Movement of the spool 45 and therefore the inner tube 12, which is frictionally fit in the spool 45, moves the distal end 16 of the inner tube 12 over the forceps' jaws 26, thus causing the forceps' jaws 26 to close. By pushing the bottom grip 53 of the pivotally mounted arm 50 toward the distal end 7 of the handle frame 5, the bifurcated end 51 of the pivotally mounted arm 50 moves toward the proximal end 8 of the handle 1. This pulls the spool 45 and the inner tube 12 toward the proximal end 8 of the handle 1. The forceps' jaws 26 and especially the ramped portions 27(a) thereof are freed from the inner tube 12, causing the jaws 26 to open. The scissor action just described is the preferred means for achieving translational motion of the inner tube 12 within the translationally stationary outer tube 11 and over the conductive leads 13.

A finger-activated safety catch or trigger 60 is provided to stop movement of the bifurcated end 51 of the arm 50 in the direction of the distal end 7 of the handle frame 5. When properly configured, the trigger 60 introduces a perset gap to prevent complete closure of the forceps' jaws 26. The trigger 60, preferably made out of a medical grade plastic, such as a 20% glass filled polycarbonate material, is crescent moon shaped with the concave side facing toward the distal end 7 of the handle frame 5 and the convex side facing toward the proximal end 8 of the handle 1. The trigger 60 has a bifurcated top with one prong of the top 64 pivotally attached to the distal end 7 of the handle frame 5 and the other prong 66 freely swinging toward the proximal end 8. The freely swinging prong 66 will loosely slide between the handle frame 5 and the bifurcated end 51 of the arm 50 when the trigger 60 is pulled, with a finger, toward the proximal end 8 of the handle 1. The freely swinging prong 66 when situated between the handle frame 5 and bifurcated end 51 stops movement toward the distal end 7 of the bifurcated end 51 and stops further translational movement of the spool 45 and inner tube 12 in the direction of the distal end 14 of the outer tube 11. This stops the inner tube 12 from sliding over the ramped portions 27(a) of the forceps' jaws 26 and, if properly configured, prevents the forceps' jaws 26 from closing completely. To allow more complete closure of the forceps' jaws 26 the trigger 60 is pushed toward the distal end 7 of the handle frame 5 removing the freely swinging prong 66 from its location between the handle frame 5 and the bifurcated end 51 of the pivotally mounted arm 50. The pivotally mounted arm 50 is then free to be pulled closer to the proximal end 8 of the handle 1. This forces the distal end 16 of the inner tube 12 to slide further over the ramped portions 27(a) of the forceps' jaws 26 and close the jaws 26 more completely.

Finally, to hold all parts of the handle 1 together, the two handle halves 5 are securely fastened together. The fit is accomplished by lining up opposing pin and hole arrangements 57 in opposing pieces 5 and ultrasonically or otherwise bonding the handle halves together along their peripheral edges.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A bipolar electrosurgical forceps comprising, in combination:
    (a) a first elongated, generally rigid tube member having a proximal end, a distal end and a lumen extending therebetween;
    (b) a second elongated tube member coaxially disposed within the lumen of said first tube member, said second tube member having a proximal end and a distal end;
    (c) a pair of conductors extending longitudinally through said second elongated tube member in side-by-side relation and insulated from one another along the length thereof, each of said pair of conductors having a proximal end and a distal end, said distal end of each of said pair of conductors being free of insulation over a first predetermined zone, the distal ends of said pair of conductors in said first zone being in parallel, face-to-face relation with respect to one another, said pair of conductors each including a second zone, contiguous to said first zone, in which said conductors are bent to create a ramp surface selectively engagable by said distal end of said second elongated tube member when said second elongated tube member is translated in the distal direction within said lumen of said first tube member;
    (d) handle means operatively coupled to said proximal end of said first tube member, said proximal end of said second tube member and said proximal ends of said pair of conductors for imparting translational, longitudinal, reciprocal motion to said second elongated tube member within said lumen of said first tube member without displacing said pair of conductors; and
    (e) means for imparting rotational movement to said first and second elongated tube members and said pair of conductors.

2. The bipolar electrosurgical forceps as in claim 1 wherein said handle means comprises a stationary element coupled to said proximal end of said first tube member and a moveable element pivotably joined to said stationary element with said moveable element having a first end coupled to said second tube member at its proximal end, and a second end of said moveable element configured for manual manipulation.

3. The bipolar electrosurgical instrument as in claim 1 and further including selectively actuatable means for limiting the extent of said translational, longitudinal reciprocal motion of said second elongated tube member.

4. The bipolar electrosurgical instrument as in claim 2 wherein said stationary element and said movable element include a scissors-style grip.

5. The bipolar electrosurgical instrument as in claim 2 and further including a trigger member operatively coupled between said stationary element and said movable element for selectively limiting the extent of movement of said movable element.

6. The bipolar electrosurgical instrument as in claim 4 wherein said handle means further includes a spool member affixed to said proximal end of said second tube member and said moveable element includes a bifurcated end for engaging said spool member.

7. The bipolar electrosurgical instrument as in claim 4 wherein said handle means further includes a knob journaled for rotation on said stationary member, said knob including means for coupling it to said second tube member whereby rotation of said knob imparts rotation to said second tube member and manual manipulation of said scissors-style grip imparts longitudinal displacement of said second tube member.

8. A bipolar electrosurgical forceps comprising, in combination:
    (a) an inner tubular member having a proximal end, a distal end and first and second lumens extending between said proximal end and said distal end;
    (b) first and second conductive wires extending through said first and second lumens, and each including a distal end portion extending beyond said distal end of said inner tubular member, said distal end portions including an electrode surface contiguous to a ramp surface;
    (c) an outer tubular member coaxially surrounding said inner tubular member, said outer tubular member being generally rigid and having a proximal end and a distal end and an outside diameter sufficiently small to pass through a cannula; and
    (d) handle means coupled to said proximal ends of said inner and outer tubular members for reciprocally displacing said inner tubular member within said outer tubular member while restraining said first and second conductive wires from longitudinal displacement, said distal end of said inner tubular member engagable with said ramp surface for effecting opening and closing of said electrode surfaces relative to one another.

9. A bipolar electrosurgical forceps as in claim 8 and further including means affixed to said proximal end of said outer tubular member and journaled for rotation on said handle means and operatively coupled to said inner tubular member for rotating said inner tubular member relative to said handle.

10. The bipolar forceps as in claim 8 and further including means for applying an RF voltage to said first and second conductive wires.

11. The bipolar electrosurgical instrument as in claim 8 wherein said handle means includes:
    (a) a stationary arm;
    (b) a moveable arm pivotally journaled to said stationary arm; and
    (c) means for coupling said inner tubular member to said moveable arm.

12. The bipolar electrosurgical instrument as in claim 11 and further including a finger-operated trigger coupled between said stationary arm and said movable arm for selectively limiting the extent of movement of said movable arm relative to said stationary arm.

13. The bipolar electrosurgical instrument as in claim 11 wherein said means for coupling comprises a spool-shaped member having a cylindrical central segment of a first outside diameter with annular flanges on opposed ends of said central segment, said flanges of a diameter larger than said predetermined diameter, said moveable arm including a bifurcated end portion for straddling said central segment between said annular flanges, said spool-shaped member including a longitudinal bore in which said proximal end of said inner tubular member is received.

14. The bipolar electrosurgical instrument as in claim 13 wherein said stationary arm and said moveable arm each including a scissors-type grip.

* * * * *